United States Patent [19]

Tomita et al.

[11] Patent Number: 4,709,062

[45] Date of Patent: Nov. 24, 1987

[54] GLYCIDYL COMPOUND

[75] Inventors: Haruo Tomita, Kobe; Yasuo Okamoto, Okayama; Kazuya Yonezawa, Kobe, all of Japan

[73] Assignee: Kanegafuchi Kagaku Kogyo Kabushiki Kaisha, Osaka, Japan

[21] Appl. No.: 823,410

[22] Filed: Jan. 28, 1986

Related U.S. Application Data

[63] Continuation-in-part of Ser. No. 681,249, Dec. 13, 1984, abandoned.

[30] Foreign Application Priority Data

Dec. 15, 1983 [JP] Japan ................... 58-237493

[51] Int. Cl.$^4$ .......................................... C07D 303/46
[52] U.S. Cl. .................................................. 549/553
[58] Field of Search ........................................ 549/553

[56] References Cited

U.S. PATENT DOCUMENTS 3,951,983 4/1976 Danilewicz et al. ............... 549/553

Primary Examiner—Norma S. Milestone
Attorney, Agent, or Firm—Antonelli, Terry & Wands

[57] ABSTRACT

A glycidyl compound having the formula (I):

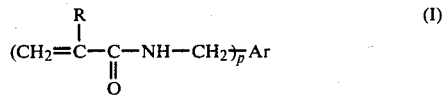

wherein R is hydrogen atom or methyl group, p is an integer of 1 to 4 and Ar is aromatic hydrocarbon group selected from the group consisting of groups having the formula (II), (III) and (IV):

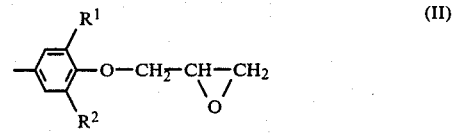

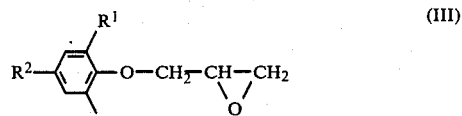

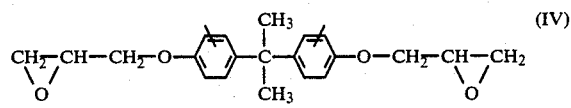

wherein $R^1$ $R^2$ are the same or different and each is an alkyl group having 1 to 4 carbon atoms.

The glycidyl compound can be cured by either heat, radical initiators or irradiation of ultraviolet rays and curing compounds prepared by using the glycidyl compound have high heat resistance and high surface hardness.

2 Claims, 4 Drawing Figures

GLYCIDYL COMPOUND

CROSS-REFERENCE TO RELATED APPLICATION

This is a continuation-in-part of application Ser. No. 681,249 filed on Dec. 13, 1984, which application is now abandoned.

BACKGROUND OF THE INVENTION

The present invention relates to a glycidyl compound having acrylamide or methacrylamide group.

Recently, epoxy resins have been widely employed in the fields of adhesives, paints, electric or electronic industry, civil engineering, and so on. Monomers or oligomers having acryloyl or methacryloyl group cure in a short time by irradiation of ultraviolet rays or electron rays, and therefore have been widely utilized in the fields of printings, coatings, photoresists, and the like.

An object of the present invention is to provide a glycidyl compound which can be cured by either irradiation of ultraviolet rays, radical initiators or curing agents, and therefore employed as a curing epoxy resin.

This and other objects of the present invention will become apparent from the description thereof.

SUMMARY OF THE INVENTION

In accordance with the present invention, there is provided a glycidyl compound having the formula (I):

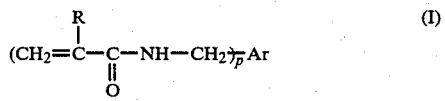

(I)

wherein R is hydrogen atom or methyl group, p is an integer of 1 to 4 and Ar is an aromatic hydrocarbon group selected from the group consisting of groups having the formulas (II), (III) and (IV):

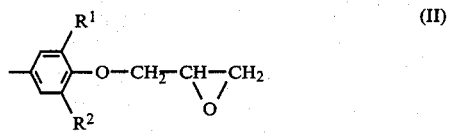

(II)

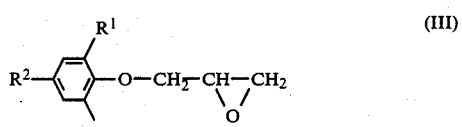

(III)

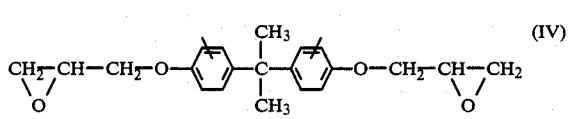

(IV)

wherein $R^1$ and $R^2$ are the same or different and each is an alkyl group having 1 to 4 carbon atoms.

DETAILED DESCRIPTION

Figure 1:
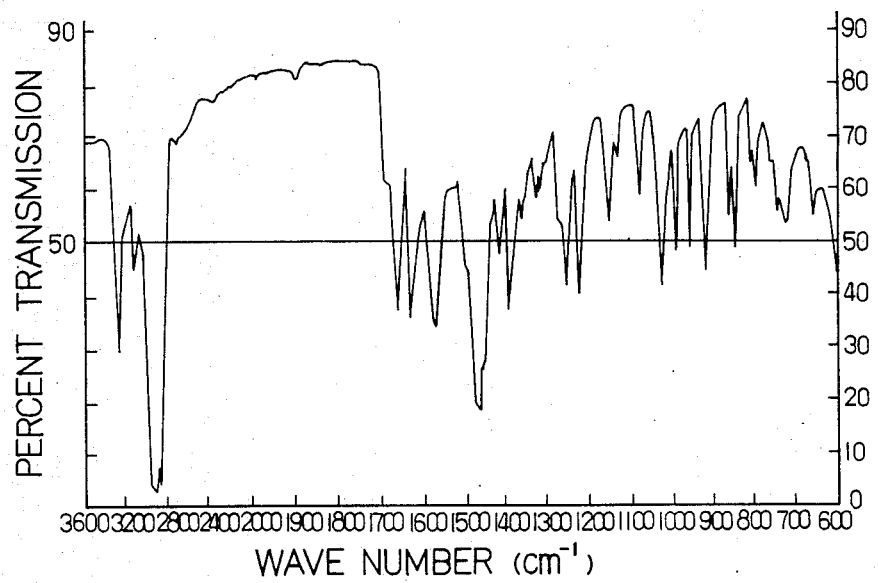
FIG. 1 is an infrared absorption spectrum of the glycidyl compound prepared in Example 1.

The glycidyl compound (I) of the present invention can be prepared with good yield by subjecting to the addition reaction of a compound having the formula (I'):

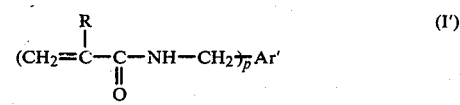

(I')

wherein R and p are as defined above and Ar' is an aromatic hydrocarbon group selected from the group consisting of groups of the formulas (II'), (III') and (IV'):

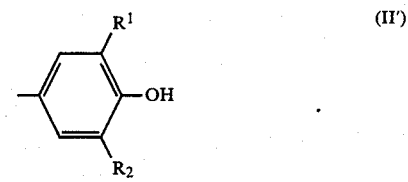

(II')

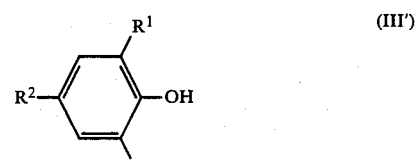

(III')

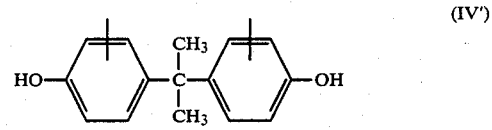

(IV')

wherein $R^1$ and $R^2$ are as defined above and an epihalohydrine, and then dehydrohalogenating the addition product with an alkali without substantial hydrolysis reaction of amide groups.

The compound having the formula (I') can be obtained by condensation of an aromatic hydrocarbon having the formula (II''), (III'') or (IV''):

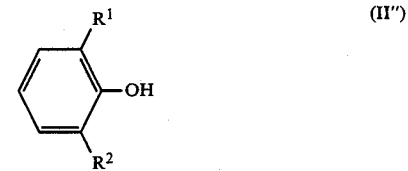

(II'')

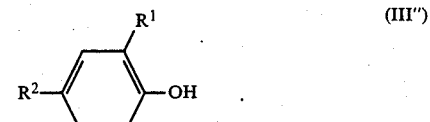

(III'')

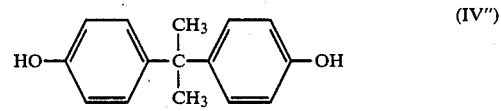

(IV'')

wherein $R^1$ and $R^2$ are as defined above and N-methylol acrylamide or N-methylol methacrylamide, or alkyl ether derivatives of the N-methylol acrylamide or N-methylol methacrylamide (hereinafter referred to as "N-methylol acrylamide compounds") in the presence of an acid as a catalyst without difficulty.

Typical examples of such aromatic hydrocarbon are, for instance, 2,6-xylenol, 2,4-xylenol, 2,2-bis(4hydroxyphenyl)propane (bisphenol A), and the like.

In accordance with the present invention, the novel glycidyl compound (I) can be obtained by converting hydroxyl group of the compound (I') into a glycidylether group with an epihalohydrin.

For instance, in case that 2,6-xylenol and N-methylol acrylamide compounds are employed as starting materials, a glycidyl compound having the formula (V):

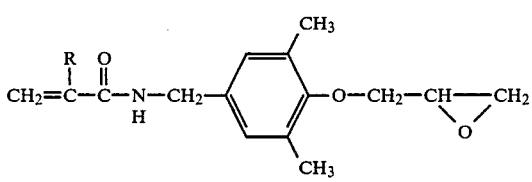

wherein R is hydrogen atom or methyl group can be obtained.

In case that 2,4-xylenol and N-methylol acrylamide compounds are employed as starting materials, a glycidyl compound having the formula (VI):

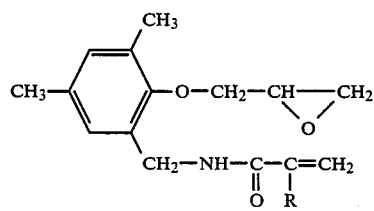

wherein R is hydrogen atom or methyl group can be obtained.

In case that bisphenol A and N-methylol acrylamide compounds are employed as starting materials, a glycidyl compound having the formula (VII):

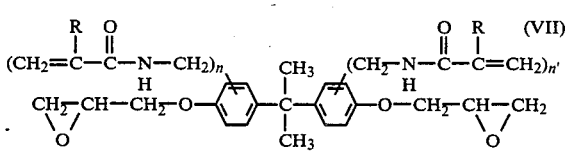

wherein R is hydrogen atom or methyl group, n and n' are each 0, 1 or 2 and at least one of n and n' is not zero.

In such case, the obtained product is a mixture of compounds having the forumulas:

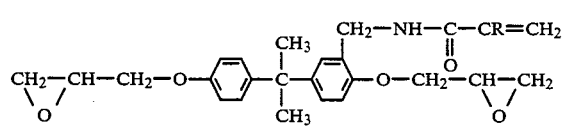

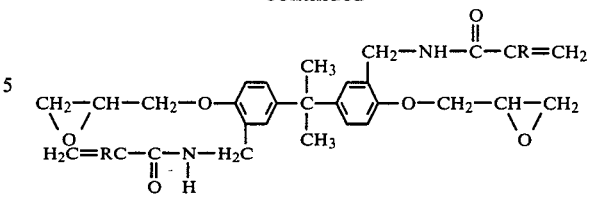

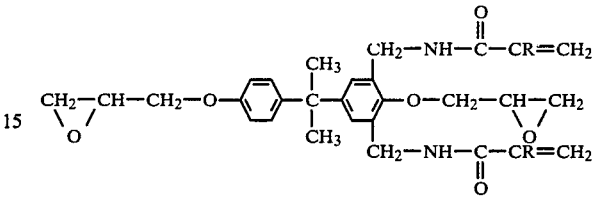

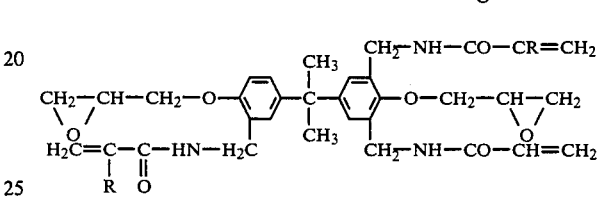

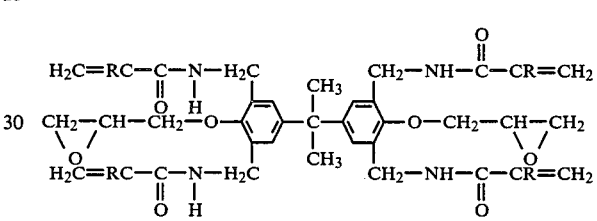

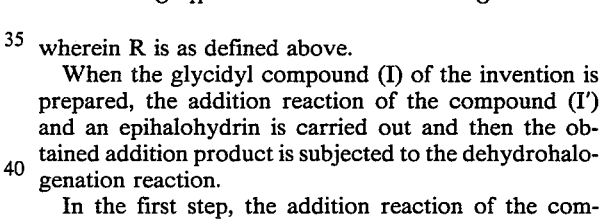

wherein R is as defined above.

When the glycidyl compound (I) of the invention is prepared, the addition reaction of the compound (I') and an epihalohydrin is carried out and then the obtained addition product is subjected to the dehydrohalogenation reaction.

In the first step, the addition reaction of the compound having the formula (I') and an epihalohydrin is carried out in the presence of a phase transfer catalyst. An amount employed of the epihalohydrin is not less than equimolar, preferably in an amount of 3 to 6 times the molar amount of the used compound having the formula (I'). A non-reactive solvent may be employed in the reaction.

Epichlorohydrin, epibromohydrin and epiiodohydrin are employed as an epihalohydrin.

Representative examples of the phase transfer catalyst are, for instance, quaternary ammonium salts such as tetrabutylammonium bromide, trioctylmethylammonium chloride and benzyltriethylammonium chloride; quaternary phosphonium salts such as tetraphenylphosphonium chloride and triphenylmethylphosphonium chloride; quaternary arsonium salts; and the like. The phase transfer catalyst is employed in an amount of 0.01 to 100% by mole, preferably 0.05 to 10% by mole based on the compound having the formula (I'). The reaction is carried out at a temperature of 50° to 120° C. for 5 minutes to 2 hours, preferably at a temperature of 80° to 110° C. for 10 to 30 minutes.

In the second step, dehydrohalogenation is carried out by using a caustic alkali such as sodium hydroxide, potassium hydroxide, lithium hydroxide, or the like. The caustic alkali can be employed in a form of solid or aqueous solution. As a catalyst used in the dehydrohalogenation, the phase transfer catalyst employed in the first step of the process can be employed as it is. When further catalyst is needed, phase transfer catalyst may be newly added. In that case, in addition to the above-mentioned phase transfer catalysts, crown ethers, ethyleneglycol, diethyleneglycol, triethyleneglycol, tetraethyleneglycol, polyethyleneglycol, and the like can be added.

The caustic alkali is employed in an equimolar or larger amount, preferably in an amount of 1.1 to 1.5 times the molar amount of the employed compound (I'). The reaction is conducted at a temperature of 20° to 90° C. for 10 minutes to 3 hours, preferably at a temperature of 40° to 70° C. for 30 minutes to 2 hours.

After the completion of the reaction, the produced salt is removed by washing the reaction mixture with water, and the unreacted epihalohydrin is distilled away from the reaction mixture to give a desired glycidyl compound of the present invention represented by the formula (I) is obtained in high purity.

The glycidyl compound of the present invention represented by the formula (I) is viscous liquid or solid at ordinary temperature, and can be cured by either heat, radical initiators or irradiation of ultraviolet rays. By their combination, curing products having high heat resistance and high surface hardness can be obtained.

The present invention is more specifically described and explained by means of the following Examples. It is to be understood that the present invention is not limited to the Examples, and various changes and modifications might be made in the invention without departing from the spirit and scope thereof.

EXAMPLE 1

A mixture of 102.6 g (0.5 mole) of 4-acrylamidemethyl-2,6-dimethylphenol, 181 g (1.96 moles) of epichlorohydrin and 2.27 g (0.01 mole) of benzyltriethylammonium chloride was agitated at 92° C. for 10 minutes. The reaction mixture was cooled to 45° C., and thereto was added dropwise 125 ml of 5N sodium hydroxide solution (0.625 mole of sodium hydroxide) with agitation for 10 minutes, and then agitated one hour at a temperature of 45° to 50° C. After the reaction mixture was cooled to room temperature, 100 ml of methylene chloride and 500 ml of water were added to the mixture to separate the mixture into two layers. The mixture having two layers was vigorously agitated and allowed to stand to separate into two layers. The organic layer separated was washed 3 times with 300 ml of water, and dehydrated by glauber's salt. Methylene chloride and epichlorohydrin were distilled away under reduced pressure to give 126 g of a light brown solid product.

Figure 2:
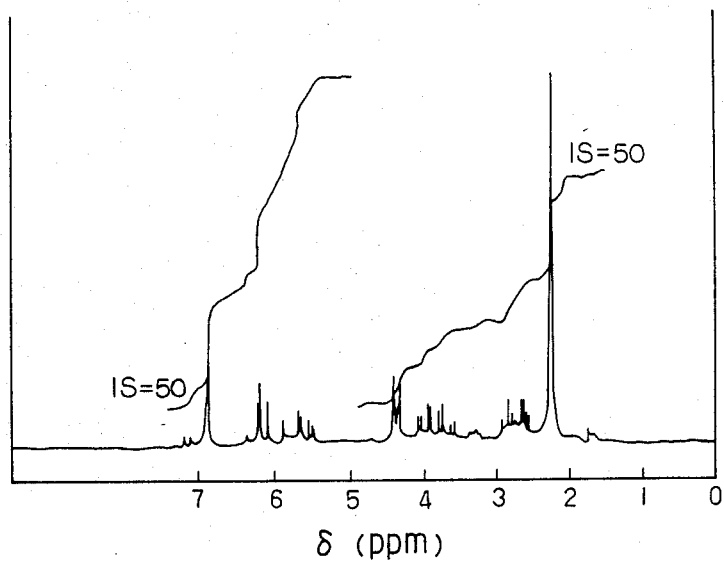
FIG. 2 is a $^1$H NMR spectrum of the glycidyl compound prepared in Example 1.

The product was purified by recrystallization from a mixed solvent of toluene and n-hexane to give 113 g of colorless needle crystal of mp 96° to 98° C. An infrared absorption spectrum of the obtained product is shown in FIG. 1 and a $^1H$ NMR spectrum of the obtained product is shown in FIG. 2 (in $CDCl_3$, standard: TMS). It was confirmed that the compound was N-(4-glycidyloxy-3,5-dimethylbenzyl)acrylamide from the infrared absorption spectrum and the $^1H$ NMR spectrum (the compound is corresponding to one having the formula (V) wherein R is hydrogen atom).

Elementary Analysis:
Found (%) : C 69.14 H 7.42 N 5.41. Calcd. (%): C 68.94 H 7.33 N 5.36.

An epoxy equivalent of the product measured by HCl-pyridine method was 258 (calculated value: 261).

A mixture of 100 g of the obtained glycidyl compound, 58 g of 3,6-endomethylene-1,2,3,6-tetrahydromethylphthalic anhydride (commercially available under the commercial name "Methylhimic Anhydride"), 0.7 g of benzyldimethylamine and 3 g of t-butylperbenzoate was cured at 150° C. for 1 hour. The cured product had a heat deflection temperature of 186° C. (ASTM D-648), a flexural strength of 1348 kg/cm$^2$, a flexural modulus of elasticity of 43000 kg/cm$^2$ and an Izod impact strength of 3.4 kg cm/cm$^2$ (noched).

A mixture of 100 g of the obtained glycidyl compound, 16 g of isophoronediamine and 3 g of t-buthylperbenzoate was cured at 150° C. for 1 hour. The cured product had a heat deflection temperature (ASTM D-648) of 182° C., a flexural strength of 1565 kg/cm$^2$ and a flexural modulus of elasticity of 41000 kg/cm$^2$.

A mixture of 100 g of the obtained glycidyl compound, 16 g of isophoronediamine and 4 g of benzoinethylether was heated to 70° C. to dissolve. The mixture was coated on a mild steel board in thickness of 50 μm, and irradiated with an ultraviolet lamp of 400 W for 30 minutes to give a film having a surface hardness (JIS K 5400) of H to HB. The film was subjected to the curing treatment at 150° C. for 15 hours to give a curing film having a surface hardness of 8H to 9H.

EXAMPLE 2

A flask equipped with a condenser and a stirrer was charged with 122 g of 2,4-dimethylphenol, 101 g of N-methylolacrylamide, 1.80 g of p-toluenesulfonic acid and 100 ml of acetone, and the mixture was reacted at 60° C. for 60 minutes with stirring. The obtained reaction mixture was poured into excess water to separate an organic layer. The organic layer was dissolved in 200 ml of methylene chloride, which was washed with three 100 ml portions of water to give 174 g of N-(3,5-dimethyl-2-hydroxybenzyl)acrylamide.

A mixture of 10.3 g (50 mmoles) of N-(3,5-dimethyl-2-hydroxybenzyl)acrylamide, 18.1 g (196 mmoles) of epichlorohydrin and 0.23 g (1 mmole) of benzyltriethylammonium chloride was agitated at 90° to 95° C. for 30 minutes. Then the reaction mixture was cooled to 50° C., and thereto was added dropwise 12.5 ml of 5N sodium hydroxide solution (62.5 mmoles of sodium hydroxide) for 10 minutes.

After the reaction was carried out at 50° C. for 1 hour and the reaction mixture was cooled to room temperature, 20 ml of methylene chloride was added to the reaction mixture, which was washd by a separating funnel according to the conventional method. The solvent and epichlorohydrine were distilled away from the organic layer under reduced pressure to give 10.8 g of a light brown solid product.

An epoxy equivalent of the obtained product measured by HCl-pyridine method was 278 and a melting point of the product was 85° to 90° C.

A mixture of 10 g of the obtained glycidyl compound, 5.8 g of methylhimic anhydride, 0.07 g of benzyldiemthylamine and 0.15 g of t-butylperbenzoate was cured at 150° C. for 1 hour. The obtained cured product had a heat deflection temperature of 158° C. (ASTM D-648).

EXAMPLE 3

There were condensed 114 g of bisphenol A and 101 g of N-methylol acrylamide (1 : 2 by molar ratio) in 100 ml of acetone in the presence of hydrochloric acid as a catalyst at a temperature of 60° C. for 60 minutes in the same manner as in Example 2 to give a condensate.

A mixture of 39 g of the condensate, 60 g of epichlorohydrin and 1.14 g of benzyltriethylammonium chloride was agitated at 95° C. for 30 minutes. The reaction mixture was cooled to 50° C., and thereto was added dropwise 50 ml of 5N sodium hydroxide solution with agitation for 10 minutes. Thereafter the reaction mixture was agitated for one hour at a temperature of 45° to 50° C., the mixture was subjected to the after-treatment in the same manner as in Example 1 to give 36 g of a light brown solid product.

Figure 3:
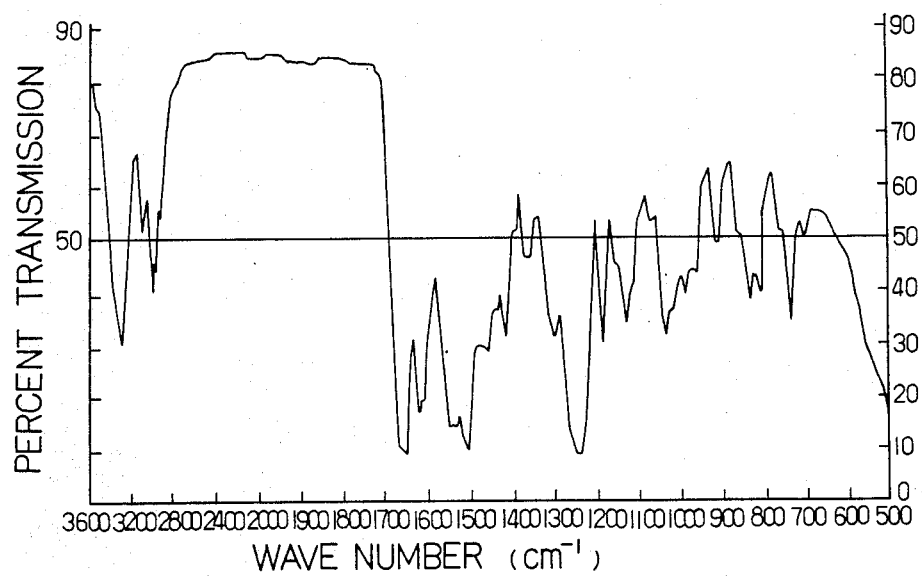
FIG. 3 is an infrared absorption spectrum of the glycidyl compound prepared in Example 3.

An infrared absorption spectrum of the obtained product is shown in FIG. 3. A softening point was 60° to 70° C., and an epoxy equivalent of the product measured by HCl-pyridine method was 227. A $^1$H NMR spectrum of the obtained product and the infrared absorption spectrum showed that the product was a mixture of compounds having the formulas:

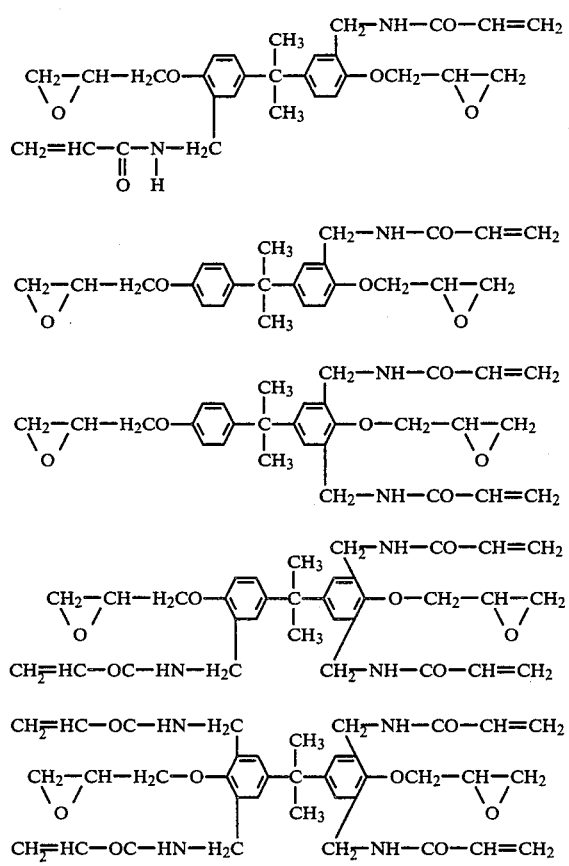

A mixture of 10 g of the obtained glycidyl compounds, 9.0 g of methylhimic anhydride, 0.5 g of benzyldimethylamine and 0.5 g of t-butylperbenzoate was cured at 100° C. for 3 hours, and thereafter at 150° C. for 15 hours. The cured product had a heat deflection temperature of 136° C. (ASTM D-648).

COMPARATIVE EXAMPLE 1

A flask was charged with 108 g of o-cresol, 101 g of N-methylolacrylamide, 5 g of 37% aqueous hydrochloric acid solution and 100 ml of acetone, and the mixture was subjected to the condensation reaction at 60° C. for 60 minutes with stirring. The obtained reaction mixture was poured into excess water to separate an organic layer. The organic layer was dissolved in 200 ml of methylene chloride, which was washed with three 100 ml portions of water to give 127 g of N-(3-methyl-4-hydroxybenzyl)acrylamide.

A mixture of 29.4 g of the condensate, 54.4 g of epichlorohydrin and 0.7 g of benzyltriethylammonium chloride was agitated at a temperature of 90° to 95° C. for 15 minutes. The resulting reaction mixture was cooled to 43° C., and thereto was added dropwise 37 ml of 5N sodium hydroxide solution with agitation for 10 minutes. Thereafter the reaction mixture was agitated for one hour at a temperature of 45° to 50° C., the mixture was subjected to the after-treatment in the same manner as in Example 1 to give 28.5 g of a light brown viscous liquid product.

An epoxy equivalent of the product measured by HCl-pyridine method was 274.

Figure 4:
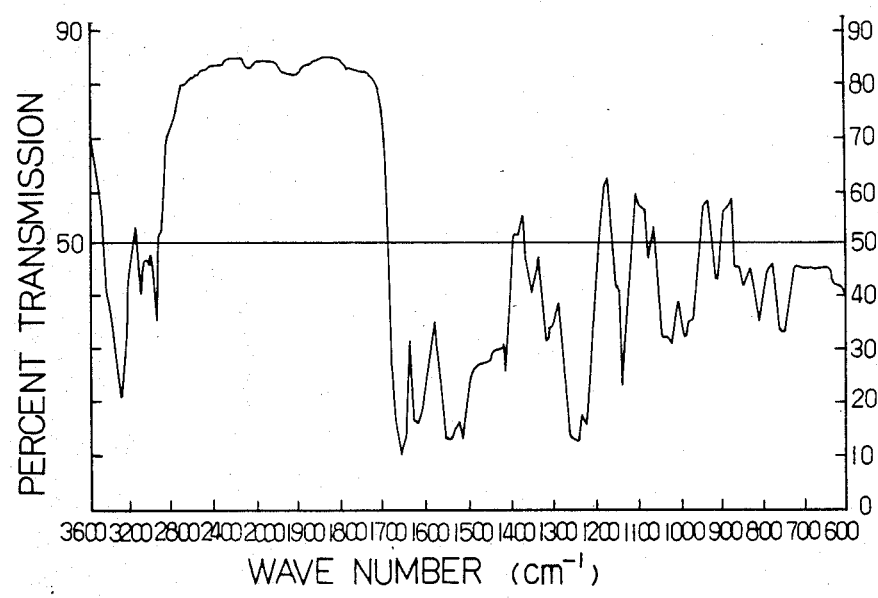
FIG. 4 is an infrared absorption spectrum of th glycidyl compound prepared in Comparative Example 1.

An infrared absorption spectrum of the obtained product is shown in FIG. 4. A $^1$H NMR spectrum of the obtained product and the infrared absorption spectrum showed that the product was N-(4-glycidyloxy-3-methylbenzyl)acrylamide having the formula:

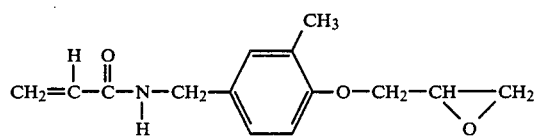

There were added 0.7 part by weight of benzylamine, 58 parts by weight of methylhimic anhydride and 1.5 parts by weight of t-butylperbenzoate to 100 parts by weight of the obtained glycidyl compound [N-(4-glycidiloxy-3-methylbenzyl)acrylamide]. After kneading, the mixture was cured at, 150 ° C. for 1 hour. The cured product had a heat deflection temperature of 128° C.

What we claim is:

1. A glycidyl compound having the formula (I):

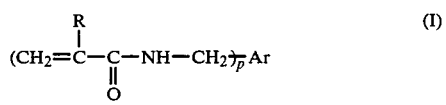

wherein R is hydrogen atom or methyl group, p is an integer of 1 and Ar is an aromatic hydrocarbon group selected from the group consisting of groups having the formulae (II) and (III):

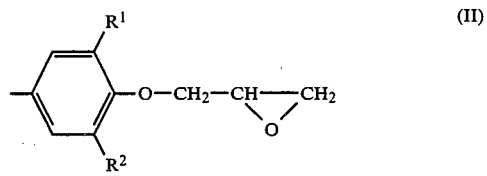

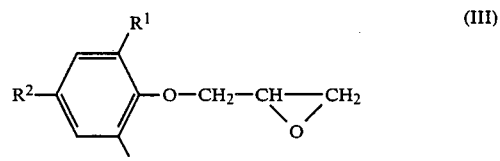

wherein $R^1$ and $R^2$ are the same or different and each is an alkyl group having 1 to 4 carbon atoms.

2. Glycidyl compounds having the formula (VII):

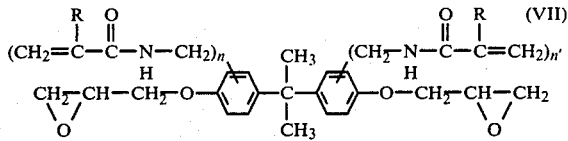

wherein R is hydrogen atom or methyl group, n and n' are 0, 1 or 2 and at least one of n and n' is not 0, said compounds (VII) being prepared by condensing bisphenol A with an N-methylol arylamide compound in the presence of an acid, adding an epihalohydrin to the condensate in the presence of a phase transfer catalyst, and dehydrohalogenating the addition product with an alkali.

* * * * *